(12) United States Patent
Love

(10) Patent No.: US 6,845,771 B1
(45) Date of Patent: Jan. 25, 2005

(54) ESSENTIAL OIL VAPORIZER

(76) Inventor: Ronald Charles Love, 15069 Grove St., Healdsburg, CA (US) 95448

( * ) Notice: Subject to any disclaimer, the term of this patent is extended or adjusted under 35 U.S.C. 154(b) by 0 days.

(21) Appl. No.: 10/141,218

(22) Filed: May 7, 2002

(51) Int. Cl.[7] ............................................. A61M 15/00
(52) U.S. Cl. ............................. 128/203.12; 128/203.23; 128/203.26; 122/4 R; 392/386; 261/DIG. 65
(58) Field of Search ...................... 128/200.14–200.23, 128/200.24, 202.21, 203.12, 203.16, 203.23, 203.26, 203.27, 204.13, 204.14, 204.17; 122/4 A, 7 B, 13.01, 13.3–19.2, 22–25, 4 R; 392/386, 391, 393; 261/DIG. 65

(56) References Cited

U.S. PATENT DOCUMENTS

| | | | | | |
|---|---|---|---|---|---|
| 1,071,389 | A | * | 8/1913 | Blosser .................. | 128/203.26 |
| 4,113,809 | A | * | 9/1978 | Abair et al. .................. | 261/81 |
| 4,369,991 | A | * | 1/1983 | Linder ......................... | 285/38 |
| 4,566,450 | A | * | 1/1986 | Brossman, Jr. ......... | 128/200.11 |
| 4,976,259 | A | * | 12/1990 | Higson et al. ......... | 128/200.18 |
| 5,054,477 | A | * | 10/1991 | Terada et al. .......... | 128/200.14 |
| 5,186,164 | A | * | 2/1993 | Raghuprasad .......... | 128/200.14 |
| 5,195,514 | A | * | 3/1993 | Liu et al. ................ | 128/203.17 |
| 5,699,786 | A | * | 12/1997 | Oshima et al. ......... | 128/200.21 |
| 2003/0075177 | A1 | * | 4/2003 | Balch et al. ............ | 128/203.26 |
| 2003/0136407 | A1 | * | 7/2003 | Matsuyama ............ | 128/203.16 |

* cited by examiner

*Primary Examiner*—Glenn K. Dawson
(74) *Attorney, Agent, or Firm*—Risto A. Rinne, Jr.

(57) ABSTRACT

An apparatus for the inhalation of a vaporized essential oil includes a container where the essential oil is adapted to be disposed. A conduit is exposed to ambient air at one end and is disposed in the container above the essential oil at a remaining end. A path is provided through which air can be drawn into the conduit, exit from the conduit and mix with a vaporized essential oil in the container, and then be inhaled. According to a first modification a detachable canister is attached to a base block. According to a second modification, a modified base block is adapted for use with existing types of pipes.

9 Claims, 2 Drawing Sheets

ESSENTIAL OIL VAPORIZER

BACKGROUND OF THE INVENTION

1. Field of the Invention

The present invention, in general relates to devices for the inhalation of vapors and, more particularly, to devices that are adapted to vaporize an essential oil of an organic substance prior to its inhalation.

There are a great many organic substances from which an essential oil can be extracted. If the essential oil is heated sufficiently, the essential oil will experience a change of state from a liquid into a gaseous state (i.e., a vapor) and will do so without any combustion occurring.

The vaporized essential oil can then be inhaled to provide a great variety of benefits without inhaling the toxic components that would be present if combustion occurred.

Discovering the medicinal and therapeutic benefits of inhaled vaporized essential oils is likely to become a leading-edge technology. There are enormous varieties of plants from which an essential oil can be extracted, vaporized, and then inhaled. The benefits of but a few of them are only partially understood, at best. With the passage of time it is almost for certain that many benefits, some moderate and some profound, will be discovered appertaining to the inhalation of various types of vaporized essential oils. If benefit is possible through pulmonary entry (i.e., the lungs), the instant invention applies.

To cite but a few candidate essential oils for use with the instant invention, Elecampane, Thyme, and Eucalyptus are compounds that may be useful in treating lung problems. It is important to understand that the essential oil that is inhaled can also be used to treat any deficiency or malady, including those that do not involve pathos of the lungs. In such instances, the lungs provide an alternate path of entry for the active ingredients of the essential oil into the bloodstream, from which any organ can be affected as desired or intended. This is described in greater detail hereinafter.

One possible benefit regarding the use of essential oils is that they may be easier to measure and therefore to set standards or regulate for consistency of quality (i.e., potency). Therefore the potential quality from one batch of essential oil as compared to another batch can be held to as tight a tolerance as desired and as allowed by technology. Accordingly, a user may be assured of a far more uniform quality when using essential oils as compared to using the raw plant material, the quality of which varies widely depending upon where it was extracted and many other factors.

As but one example of the potential use of an essential oil, there are currently well known medicinal uses for marijuana (i.e., hemp) when the essential oil components are inhaled. It can be used to treat various psychological disorders and also to ameliorate pain.

A common current method for the inhalation of the essential components (i.e., active ingredients) of marijuana includes the making of a pseudo-type of a cigarette or the use of a pipe into which a quantity of selected plant material is inserted. The plant material is then combusted (i.e., a source of heat or flame is applied thereto) and the smoke that is produced by combustion is subsequently inhaled. Inhalation provides a path through the lungs and bloodstream by which the active ingredients are absorbed. However, this method incurs several disadvantages.

For one thing, such use is illegal in certain areas and is therefore prohibited. Another disadvantage is that combustion generally produces a wide spectrum of toxic and carcinogenic by-products that are harmful to inhale. The tobacco companies are quite familiar with the deleterious effects from the by-products of combustion.

However, the use of an essential oil solves many problems in that the essential oil can potentially be legally extracted from the marijuana plant, sold (perhaps by prescription), possessed, and used without violating local, state, or federal statutes. This is because certain of the statutes that regulate such use may appertain to possession of the plant per se, and not necessarily to an extract of its essential oil.

Since the essential oil is heated only to the degree necessary to vaporize it for inhalation, no combustion occurs and therefore none of the harmful compounds associated with combustion are produced or inhaled.

Also, as mentioned before the quality of an essential oil can be held to uniform standards of potency.

A known prior art device exists that is profoundly limited and is comprised essentially of a glass tube that is open at a first end and which includes an enlarged bulb at an opposite second end. A user inhales from the first end. A single small opening is provided at the top of the enlarged bulb. An essential oil is added through the opening at the top of the bulb and allowed to settle in the bottom of the bulb which is then heated to vaporize the oil for inhalation.

The first limitation is that it is difficult to add potentially expensive essential oils through the opening at the top. Spillage is likely to occur. Once the oil has been added it is then especially difficult to remove any unused portion from the bulb.

It is also especially difficult to clean the bulb (where the oil has been heated) due to limited access.

Neither is it possible to use the bulb for the clean long-term storage of the oil (because of the two openings that would tend to dry it out).

Nor is possible to use the bulb for the storage of several different types of essential oils. This is desirable for those whom, by way of necessity, can optimally benefit by the inhalation of several different vaporized essential oils.

Also, the intake path (during inhalation) does not ensure the uniform mixing of the vaporized essential oil with the intake stream of air, thereby producing unpredictable results. Sometimes too little a quantity of the vapor will be inhaled, sometimes too much will be inhaled.

Nor is there any known way of adapting an existing pipe for use with an essential oil vaporizer.

The inhalation of a vaporized essential oil may also be useful in avoiding exposure of the beneficial components (i.e., compounds) thereof to enzymes that are present in the stomach. Certain stomach enzymes may destroy or diminish the efficacy of certain compounds that are taken orally.

Inhalation provides an alternative path for the entry of these compounds or active ingredients into the bloodstream that averts contact with stomach enzymes.

Accordingly there exists today a need for an essential oil vaporizer that is easy to use and which adequately mixes the vapor with the inhalation stream and which is versatile.

Clearly, such an apparatus would be a useful and desirable device.

2. Description of Prior Art

Vaporizers are, in general, known. For example, the following patents describe various types of these devices:

U.S. Pat. No. 6,295,982 to Reed, Jr., October, 2, 2001;

U.S. Pat. No. 6,250,301 to Pate, Jun. 26, 2001;

U.S. Pat. No. 6,095,153 to Kessler, et al., Aug. 1, 2000; and

U.S. Pat. No. 4,303,083 to Burruss, Jr., Dec. 1, 1981.

While the structural arrangements of the above types of devices, at first appearance, may have similarities with the present invention, they differ in material respects. These differences, which will be described in more detail hereinafter, are essential for the effective use of the invention and which admit of the advantages that are not available with the prior devices.

OBJECTS AND SUMMARY OF THE INVENTION

It is an object of the present invention to provide an essential oil vaporizer that is easy to use.

It is also an important object of the invention to provide an essential oil vaporizer that includes a canister that is adapted to receive an essential oil.

Another object of the invention is to provide an essential oil vaporizer that includes a detachable canister that is adapted to receive an essential oil.

Still another object of the invention is to provide an essential oil vaporizer that includes a detachable canister that is easy to clean.

Still yet another object of the invention is to provide an essential oil vaporizer that includes a detachable canister that can be used for the storage of an essential oil.

Yet another important object of the invention is to provide an essential oil vaporizer that includes a plurality of detachable canisters that can be used for the storage of a plurality of essential oils.

Still yet another important object of the invention is to provide an essential oil vaporizer that is adapted for use with existing types of pipes.

Still yet a first additional important object of the invention is to provide an essential oil vaporizer that includes a method for adjusting the mixture of air and essential oil vapor prior to inhalation.

Still yet a second additional important object of the invention is to provide an essential oil vaporizer that includes a carburetor for adjusting the mixture of air and essential oil vapor prior to inhalation.

Briefly, an essential oil vaporizer that is constructed in accordance with the principles of the present invention has a conduit that extends a predetermined distance into an area where an essential oil is adapted to be heated at one end and which extends into the ambient air at an opposite end. A path is provided through which air can be drawn by partial vacuum into the conduit, mixed with a vaporized essential oil, and then inhaled. A detachable canister is shown and a base that is adapted for use with existing types of pipes is also disclosed.

DETAILED DESCRIPTION OF THE INVENTION

Figure 1:
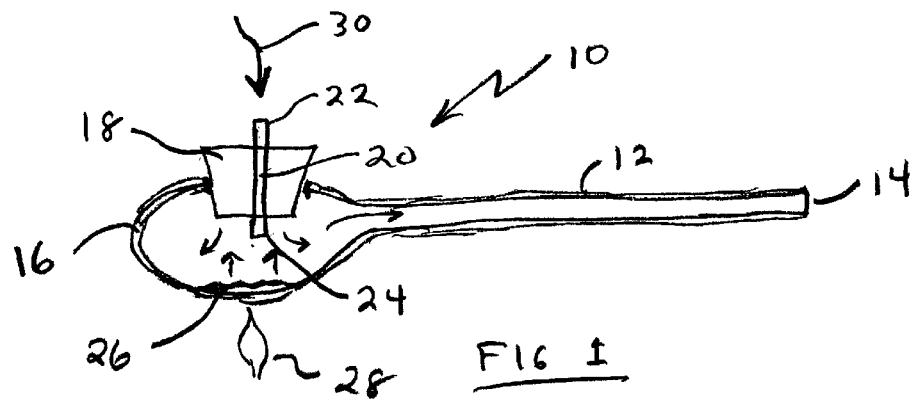
FIG. 1 is a cross sectional view of a basic version of an essential oil vaporizer.

Referring to all of the DRAWINGS and in particular to FIG. 1 is shown, an essential oil vaporizer that is identified in general by the reference numeral 10.

The vaporizer 10 includes an elongate hollow tube 12 with a first tube end 14 and an opposite end to which an enlarged bulb 16 is attached.

The bulb 16 includes a large opening at the top into which a fire resistant stopper 18 is inserted. The stopper 18 effectively seals the large opening at the top when it is pressed therein.

A conduit 20 is inserted through the stopper 18 with a first conduit end 22 exposed to ambient air and an opposite second conduit end 24 disposed a predetermined distance inside of the bulb 16 cavity.

In use, the stopper 18 is removed and an essential oil 26 is added through the large opening into the bulb 16 where it settles at the bottom thereof.

A source of heat 28 is applied to the bulb 16 under the oil 26 until at least some of the oil 26 vaporizes.

At that time a mouth of a user (not shown) surrounds the first tube end 14 and draws ambient air into the first conduit end 22 by sucking (i.e., creating a partial vacuum).

The ambient air (shown by arrow 30) enters into the first conduit end 22 and exits from the second conduit end 24 that is disposed above the oil 26.

The ambient air mixes with the vaporized essential oil 26 and the resultant mixture is drawn out through the hollow tube 12, exiting from the first tube end 14 where it is inhaled by the user. Combustion never occurs, just a heating sufficient to effect a change of state from a liquid to a gas of the essential oil 26.

The ambient air as it exits from the second conduit end 24 agitates and blends with the vaporized essential oil 26 creating an essential oil 26 and ambient air mixture. In this regard, the conduit 20 functions as a carburetor providing a desired air/oil mixture.

Figure 2:
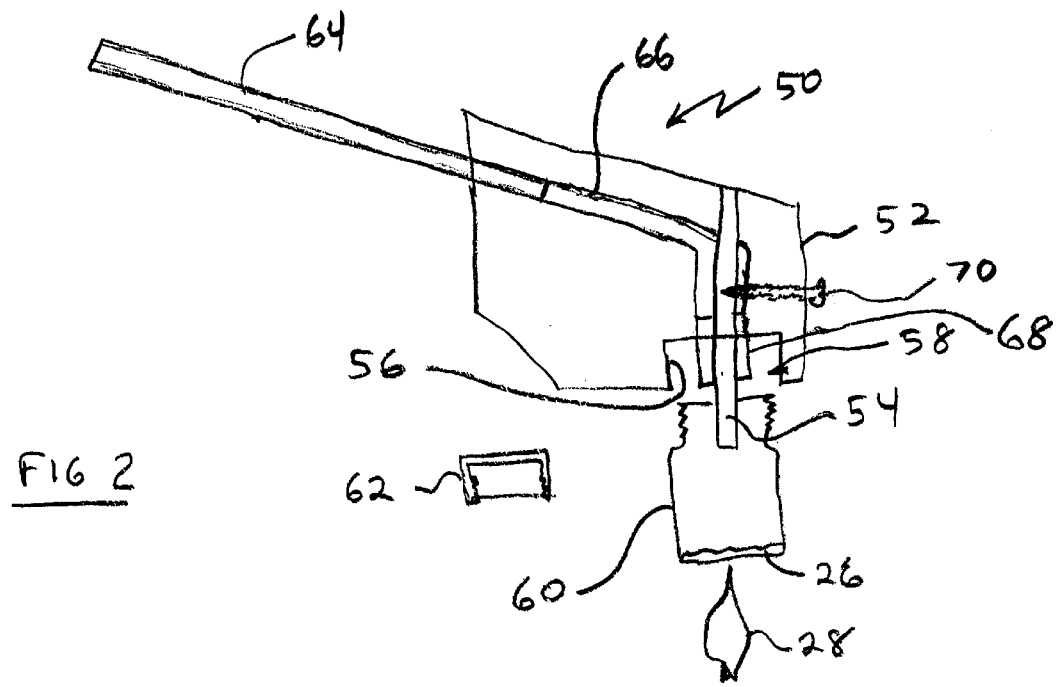
FIG. 2 is a cross sectional view of a first modified version of an essential oil vaporizer.

Referring now primarily to FIG. 2, is shown a first modified essential oil vaporizer, identified in general by the reference numeral 50.

The first modified essential oil vaporizer 50 includes a base block 52. A modified conduit 54 passes through the base block 52 with one end disposed above and below it.

A cylindrical recess 56 is provided in the bottom of the base block 52. A protruding pin 58 is pressed into one side of the cylindrical recess 56.

The pin 58 is adapted to engage the threads of a detachable canister 60, which is screwed into the cylindrical recess 56 for use and removed for storage or cleaning.

The essential oil 26 is shown in the canister 60. A lid 62 is also shown and can be used to seal the canister 60 when separate from the base block 52. This is useful for the storage of the oil 26 and a plurality of canisters 60 can be used for the storage of a plurality of types of essential oils (not shown).

A hollow inhalation tube 64 is inserted into an upper end of a channel 66 that is formed in the base block 52.

The channel 66 includes a lower end into which is inserted an extension tube 68. As shown, the lower end of the channel 66 and the extension tube 68 are disposed in a concentric orientation with respect to each other sharing the same central longitudinal axis.

The extension tube 68 extends out of the cylindrical recess 56 and into the canister 60 (when the canister 60 is fully screwed and inserted into the cylindrical recess 56) but to a lesser degree than does the modified conduit 54.

In use, the essential oil 26 is added to the canister 60, the canister 60 is screwed into the cylindrical recess 56 until seated, the source of heat 28 is applied to the bottom of the canister 60 sufficient to vaporize at least a portion of the essential oil 26 and then the user draws air (i.e., inhales) through the inhalation tube 64.

Ambient air again mixes with the vaporized essential oil 26 and the resultant mixture enters into the extension tube 68, passes through the channel 66 and enters into the inhalation tube 64, from which it exits and is inhaled.

A needle valve 70 is also threaded into the base block 52 and provides a method of increasing or decreasing the resistance of ambient air as it passes through the modified conduit 54. This is useful in attaining a better and more uniform mixture less dependent upon the force of inhalation and in regulating the speed at which the mixture can be inhaled (for safety and maximum therapeutic benefit).

Figure 3:
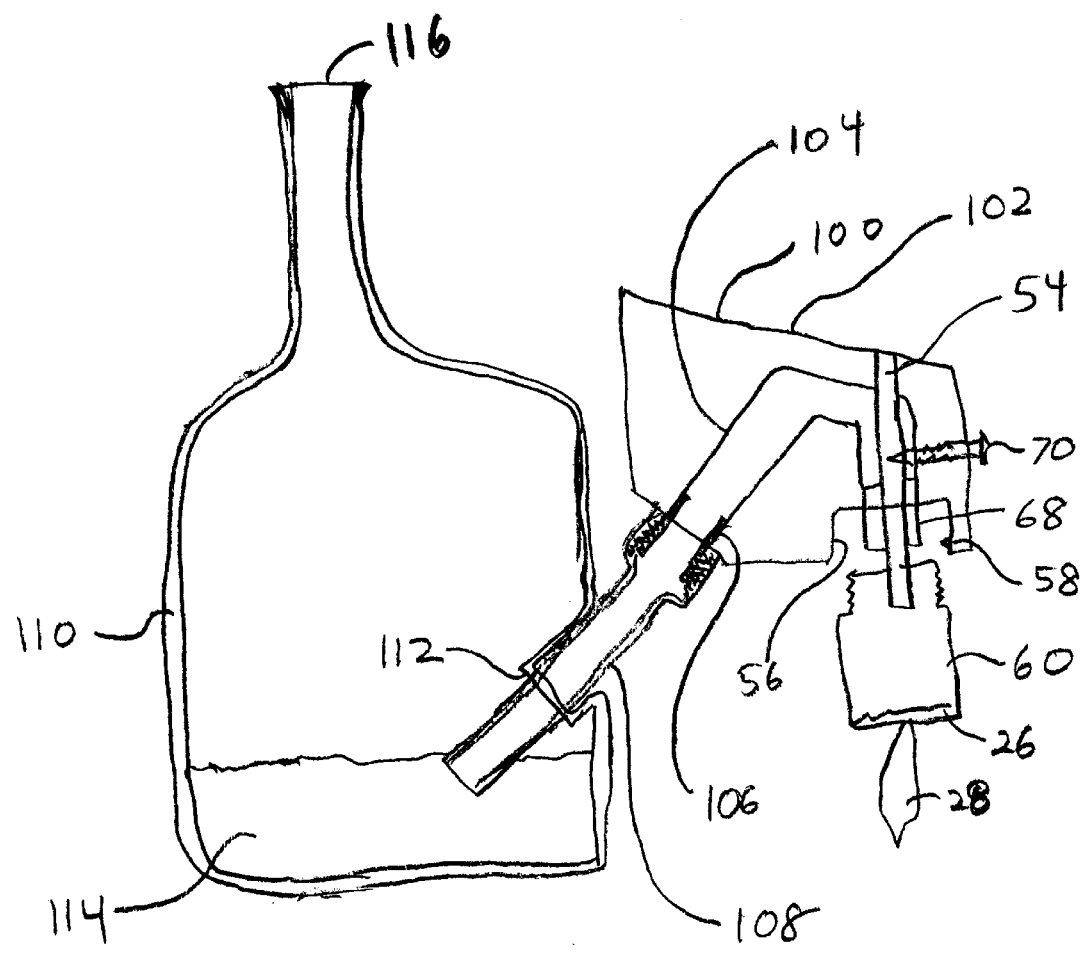
FIG. 3 is a cross sectional view of a second modified version of an essential oil vaporizer.

Referring now to FIG. 3, a second modified essential oil vaporizer, identified in general by the reference numeral 100, is shown.

The second modified essential oil vaporizer 100 includes a modified base block 102.

The modified base block 102 includes a modified channel 104 that curves within the modified base block 102 so that it exits in a generally downward direction.

An adapter tube 106 is inserted where the modified channel 104 exits.

The adapter tube 106 includes threads onto which an adapter extension tube 108 is threaded.

The adapter tube 106 and the adapter extension tube 108 are modified as desired to allow use of the modified essential oil vaporizer 100 with existing types of pipes.

As shown, a water pipe 110 is provided that includes a side opening 112 into which the adapter extension tube 108 is inserted until the modified essential oil vaporizer 100 is properly secured to the water pipe 110.

The adapter extension tube 108 is of a length sufficient so that a distal end is disposed under a quantity of water 114 that is placed in the water pipe 110.

When the essential oil 26 is vaporized, the user inhales from a top tube 116 of the water pipe 110. This forces the resultant ambient air and vaporized essential oil 26 mixture to also pass through the modified channel 104, the adapter tube 106, the adapter extension tube 108, and into the water 114.

The mixture exits from the water 114 and out of the top tube 116 of the water pipe 110 and is inhaled. The water 114 cools the mixture and also filters it to some extent.

Modifications to the adapter tube 106 and the adapter extension tube 108 allow the modified essential oil vaporizer 100 to be used with virtually any existing type of a pipe. This allows old and new pipes to benefit from the benefits of inhaling vaporized essential oils.

This increase in the utility of pipes that were originally designed for the inhalation of combusted material (i.e., smoke) and which can now be used for the inhalation of vaporized essential oils has not before been available.

Certain modifications obvious to those possessing ordinary skill have been omitted for purposes of clarity. For example, the use of a gasket intermediate the top of the canister 60 and the cylindrical recess 56 can be provided to improve the seal, as desired.

Similarly, a second gasket can be disposed around the adapter extension tube 108 and intermediate the side opening 112 to provide a better seal, as desired.

Also, the ability to store the essential oil 26 in the canister 60, to easily add or remove the essential oil 26 to or from the canister 60, and to easily clean the canister 60 are additional benefits provided by the instant invention.

Furthermore, the canister 60 can be formed out of any desired material able to withstand the heat source 28. For example, PYREX types of glass or metals are possible materials to use in the formation of the canister 60. Similarly, any other component part described herein can be formed of any desired material.

The amount of heat that is applied is also another variable. Depending on the characteristics of the essential oil 26 at ambient temperatures at typical atmospheric pressures, a very small quantity of the heat source 28 may be required. It is even possible that evaporation may provide a sufficient quantity of the vaporized essential oil 26, thereby eliminating the need for the heat source 28.

The invention has been shown, described, and illustrated in substantial detail with reference to the presently preferred embodiment. It will be understood by those skilled in this art that other and further changes and modifications may be made without departing from the spirit and scope of the invention which is defined by the claims appended hereto.

What is claimed is:

1. An essential oil vaporizer, comprising:
   (a) a container adapted to contain said essential oil;
   (b) a conduit having a first end and an opposite second end, said first end exposed to an ambient air source external with respect to said container and said second end extending into said container a predetermined distance;

(c) an inhalation path that includes a first inhalation path end beginning at said first end of said conduit, and wherein said inhalation path is adapted to draw said ambient air in from said first end of said conduit and to exit from said second end of said conduit where said ambient air is adapted to mix with at least some of said essential oil that has been vaporized to produce a mixture and wherein said mixture is adapted to exit from a second inhalation path end that is disposed away from said first inhalation path end and including a base block, said base block adapted to receive said container; and (d) wherein said container includes a canister, and wherein said canister includes means for detachably-attaching said canister with respect to said base block, and wherein said means for detachably-attaching includes thread means attached to said canister and a corresponding means of engaging said thread means, said corresponding means attached to said base block, and wherein said corresponding means includes providing a cylindrical recess in a bottom of said base block and of providing a pin disposed along a wall of said cylindrical recess and wherein said pin is adapted to engage with said thread means.

2. The essential oil vaporizer of claim 1 wherein said second end of said conduit is disposed in said canister when said canister is attached to said base block.

3. The essential oil vaporizer of claim 2 wherein said inhalation path includes a channel in said base block, said channel including an upper end and a lower end, said lower end open to said canister when said canister is attached to said base block.

4. The essential oil vaporizer of claim 3 wherein said lower end of said channel includes an extension tube, said extension tube extending from said lower end into said canister a predetermined distance away from said base block that is less than an amount said conduit extends into said canister when said canister is attached to said base block.

5. The essential oil vaporizer of claim 3 wherein said upper end of said channel is adapted to receive a hollow inhalation tube that extends away from said base block a predetermined distance.

6. The essential oil vaporizer of claim 2 wherein said base block includes a modified channel and wherein said modified channel includes a modified upper end and wherein said modified upper end includes means for adapting said base block for use with an existing pipe.

7. The essential oil vaporizer of claim 6 wherein said means for adapting said base block includes an adapter tube that is disposed at said modified upper end.

8. The essential oil vaporizer of claim 7 wherein said adapter tube is adapted to receive an adapter extension tube and wherein said adapter extension tube is adapted for insertion into said existing pipe.

9. An essential oil vaporizer, comprising:

(a) a container adapted to contain said essential oil;

(b) a conduit having a first end and an opposite second end, said first end exposed to an ambient air source external with respect to said container and said second end extending into said container a predetermined distance;

(c) an inhalation path that includes a first inhalation path end beginning at said first end of said conduit, and wherein said inhalation path is adapted to draw said ambient air in form said first end of said conduit and to exit from said second end of said conduit where said ambient air is adapted to mix with at least some of said essential oil that has been vaporized to produce a mixture and wherein said mixture is adapted to exit from a second inhalation path end that is disposed away from said first inhalation path end and including a base block, said base block adapted to receive said container; and including a stopper and wherein said conduit is disposed in said stopper and wherein said stopper is adapted to be inserted into an opening provided in a top of said container.

* * * * *